(12) United States Patent
Brackhagen et al.

(10) Patent No.: US 9,616,036 B2
(45) Date of Patent: *Apr. 11, 2017

(54) SUSTAINED RELEASE DOSAGE FORMS

(71) Applicant: Dow Global Technologies LLC, Midland, MI (US)

(72) Inventors: Meinolf Brackhagen, Walsrode (DE); Roland Adden, Walsrode (DE); Oliver Petermann, Hamburg (DE); Robert L. Sammler, Midland, MI (US); David E. Wallick, Midland, MI (US)

(73) Assignee: Dow Global Technologies LLC

( * ) Notice: Subject to any disclaimer, the term of this patent is extended or adjusted under 35 U.S.C. 154(b) by 78 days.

This patent is subject to a terminal disclaimer.

(21) Appl. No.: 14/390,046

(22) PCT Filed: Apr. 8, 2013

(86) PCT No.: PCT/US2013/035589
§ 371 (c)(1),
(2) Date: Oct. 2, 2014

(87) PCT Pub. No.: WO2013/154977
PCT Pub. Date: Oct. 17, 2013

(65) Prior Publication Data
US 2015/0057358 A1    Feb. 26, 2015

Related U.S. Application Data

(60) Provisional application No. 61/622,751, filed on Apr. 11, 2012.

(51) Int. Cl.
| | |
|---|---|
| *A61K 31/167* | (2006.01) |
| *A61K 9/20* | (2006.01) |
| *C08B 11/08* | (2006.01) |
| *C08B 11/193* | (2006.01) |
| *C08L 1/28* | (2006.01) |

(52) U.S. Cl.
CPC .......... *A61K 31/167* (2013.01); *A61K 9/2018* (2013.01); *A61K 9/2054* (2013.01); *A61K 9/2095* (2013.01); *C08B 11/08* (2013.01); *C08B 11/193* (2013.01); *C08L 1/284* (2013.01)

(58) Field of Classification Search
None
See application file for complete search history.

(56) References Cited

U.S. PATENT DOCUMENTS

| 4,001,211 A | 1/1977 | Sarkar | |
|---|---|---|---|
| 4,678,516 A * | 7/1987 | Alderman | ............ A61K 9/0014 106/15.05 |
| 4,696,762 A * | 9/1987 | Sander | .................. A23L 1/0534 252/363.5 |
| 4,734,285 A | 3/1988 | Alderman | |
| 7,666,918 B2 | 2/2010 | Prieto et al. | |

FOREIGN PATENT DOCUMENTS

| WO | 2005115330 A2 | 12/2005 |
|---|---|---|
| WO | 2012051035 A1 | 4/2012 |

OTHER PUBLICATIONS

Bartelmus, et al., Analysis of Cellulose Ether Groups, Z. Anal. Chem., 286, (1977), 161-190.
Lindberg, et al., Distribution of Substituents in O-Ethyl-O-(2-Hydrodyethyl)Cellulose, Carbohydrate Research, 176, (1988), 137-144.
Sweet, et al., Quantitative Analysis by Various G.L.C. Response-Factor Theories for Partially methylated and Partially Ethylated Alditol Acetates, Carbohydrate Research, 40, (1975), 217-225.
Ackman, Fundamental Groups in the Response of Flame Ionization Detectors to Oxygenated Aliphatic Hydrocarbons, Journal of Gas Chromatography, (1964), 173-179.
Addison, et al., Flame Ionization Detector Molar Responses for Methyl Esters of Some Polyfunctional Metabolic Acids, Journal of Gas Chromatography, 6, (1968), 135-138.

* cited by examiner

*Primary Examiner* — Dennis Heyer

(57) ABSTRACT

A sustained release dosage form comprises an active ingredient blended with a polymeric matrix. At least a portion of the polymeric matrix is formed by a cellulose ether having an onset dissolution temperature of at least 40° C., having anhydroglucose units joined by 1-4 linkages and having methyl groups, hydroxyalkyl groups, and optionally alkyl groups being different from methyl as substituents such that the cellulose ether has an MS (hydroxyalkyl) of 0.05 to 1.00, and hydroxyl groups of anhydroglucose units are substituted with methyl groups such that $[s23/s26-0.2*MS(hydroxyalkyl)]$ is 0.31 or less, wherein $s23$ is the molar fraction of anhydroglucose units wherein only the two hydroxyl groups in the 2- and 3-positions of the anhydroglucose unit are substituted with a methyl group and wherein $s26$ is the molar fraction of anhydroglucose units wherein only the two hydroxyl groups in the 2- and 6-positions of the anhydroglucose unit are substituted with a methyl group.

15 Claims, 1 Drawing Sheet

US 9,616,036 B2

SUSTAINED RELEASE DOSAGE FORMS

FIELD

This invention relates to novel sustained release dosage forms comprising certain cellulose ethers.

INTRODUCTION

Sustained release dosage forms have found wide usage in a variety of technology areas, such as in personal care or agricultural applications, water treatment and particularly in pharmaceutical applications. Sustained release dosage forms are designed to release a finite quantity of an active ingredient into an aqueous environment over an extended period of time. Sustained release pharmaceutical dosage forms are desirable because they provide a method of delivering a long-lasting dose in a single application without overdosing. Known sustained release pharmaceutical dosage forms contain a medicament or a vitamin whose rate of release is controlled by a polymeric matrix. Water-soluble cellulose ethers are known to be useful as a polymeric matrix. Water-soluble cellulose ethers hydrate on the outer tablet skin to form a gel layer. A fast formation of a gel layer is important to prevent wetting of the interior and disintegration of the tablet core. Once the gel layer is formed, it controls the penetration of additional water into the tablet. As the outer gel layer fully hydrates and dissolves, an inner layer must replace it and be sufficiently cohesive and continuous to retard the influx of water and control drug diffusion.

U.S. Pat. No. 4,734,285 discloses that the release of an active ingredient from a solid tablet can be prolonged by employing a fine particle sized hydroxypropyl methylcellulose ether composition as an excipient in the solid tablet.

In view of the high pharmaceutical importance of dosage forms that are able to release an active ingredient from a solid tablet in a controlled or sustained manner, it would be desirable to find an additional way to sustain the release of an active ingredient from a pharmaceutical dosage form.

Accordingly, one object of the present invention is to provide a new sustained release dosage form which comprises a cellulose ether as a polymeric matrix. A preferred object of the present invention is to provide a new sustained release dosage form which comprises a cellulose ether as a polymeric matrix wherein the release of the active ingredient from a solid tablet can be increased without decreasing the particle size of the cellulose ether.

SUMMARY

Surprisingly, it has been found that the release of an active ingredient from a dosage form into an aqueous environment can be extended if at least a portion of the polymeric matrix is formed by a cellulose ether wherein the ether substituents have a specific distribution pattern.

Accordingly, one aspect of the present invention is a sustained release dosage form which comprises at least one active ingredient blended with a polymeric matrix, wherein at least a portion of the polymeric matrix is formed by at least one cellulose ether having anhydroglucose units joined by 1-4 linkages and having methyl groups, hydroxyalkyl groups, and optionally alkyl groups being different from methyl as substituents such that said at least one cellulose ether has an MS (hydroxyalkyl) of 0.05 to 1.00, and hydroxyl groups of anhydroglucose units are substituted with methyl groups such that $[s23/s26-0.2*MS(\text{hydroxyalkyl})]$ is 0.31 or less, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group and wherein said at least one cellulose ether has an onset dissolution temperature of at least 40° C., measured at a concentration of 2 weight percent in water.

Another aspect of the present invention is a process for preparing a sustained release dosage form which comprises the steps of I.) blending one or more cellulose ethers, one or more active ingredients, and one or more optional adjuvants, and II.) compressing the blend to a dosage form, wherein at least one cellulose ether is a cellulose ether as defined above.

Yet another aspect of the present invention is the use of a cellulose ether as defined above for producing a sustained release dosage form.

DETAILED DESCRIPTION

Figure 1:
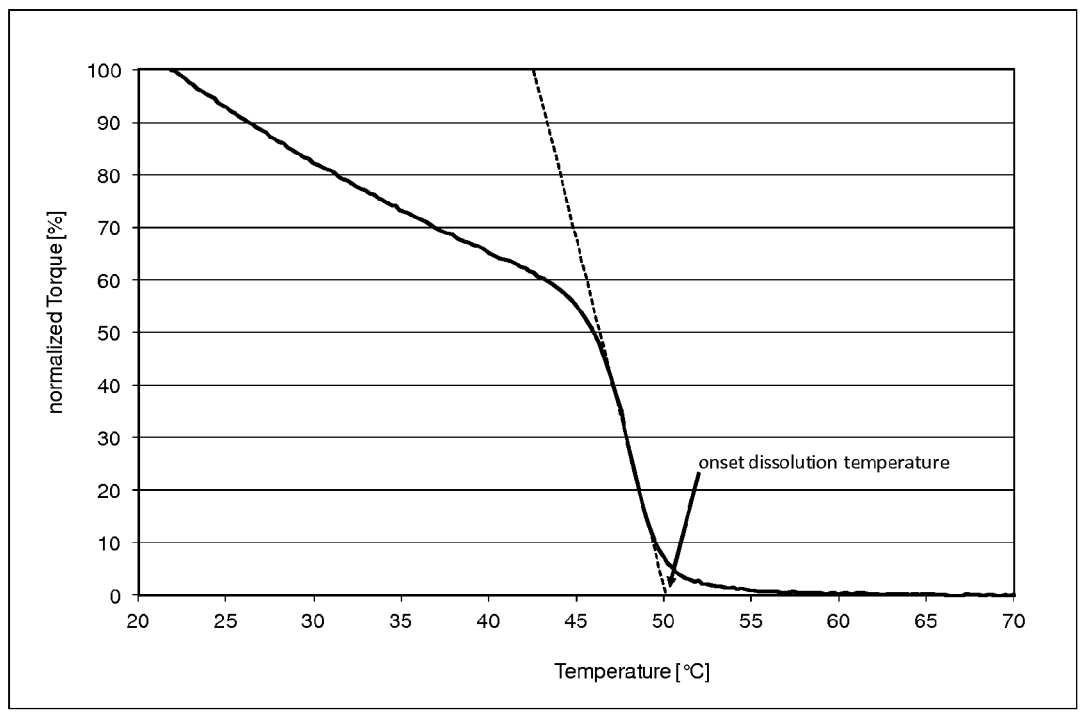
FIG. 1 is a graphical representation of how to determine the onset dissolution temperature of a cellulose ether.

At least a portion of the polymeric matrix of the sustained release dosage form is formed by at least one cellulose ether which has anhydroglucose units joined by 1-4 linkages and which has methyl groups, hydroxyalkyl groups, and optionally alkyl groups being different from methyl as substituents. The hydroxyalkyl groups can be the same or different from each other. Preferably the cellulose ether comprises one or two kinds of hydroxyalkyl groups, more preferably one or more kinds of hydroxy-$C_{1-3}$-alkyl groups, such as hydroxypropyl and/or hydroxyethyl. Useful optional alkyl groups are, e.g., ethyl or propyl, ethyl being preferred. Preferred ternary cellulose ethers are ethyl hydroxypropyl methyl celluloses, ethyl hydroxyethyl methyl celluloses, or hydroxyethyl hydroxypropyl methyl celluloses. Preferred cellulose ethers are hydroxyalkyl methyl celluloses, particularly hydroxy-$C_{1-3}$-alkyl methyl celluloses, such as hydroxypropyl methylcelluloses or hydroxyethyl methylcelluloses.

An essential feature of the cellulose ether is its unique distribution of methyl groups on the anhydroglucose units such that $[s23/s26-0.2*MS(\text{hydroxyalkyl})]$ is 0.31 or less, or 0.30 or less, or 0.27 or less, or 0.25 or less, or 0.23 or less or 0.21 or less. Typically $[s23/s26-0.2*MS(\text{hydroxyalkyl})]$ is 0.07 or more, more typically 0.10 or more, and most typically 0.13 or more. As used herein, the symbol "*" represents the multiplication operator.

In the ratio s23/s26, s23 is the molar fraction of anhydroglucose units wherein only the two hydroxyl groups in the 2- and 3-positions of the anhydroglucose unit are substituted with methyl groups and s26 is the molar fraction of anhydroglucose units wherein only the two hydroxyl groups in the 2- and 6-positions of the anhydroglucose unit are substituted with methyl groups. For determining the s23, the term "the molar fraction of anhydroglucose units wherein only the two hydroxyl groups in the 2- and 3-positions of the anhydroglucose unit are substituted with methyl groups" means that the 6-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups. For determining the s26, the term "the molar fraction of anhydroglucose units wherein only the two hydroxyl groups in the 2- and 6-positions of the anhydroglucose unit are substituted with methyl groups" means that the 3-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups.

The term "hydroxyl group substituted with methyl group" or "hydroxyl group substituted with hydroxyalkyl group" as used herein means that the hydrogen atom on the hydroxyl group is replaced by a methyl group or a hydroxyalkyl group.

Formula I below illustrates the numbering of the hydroxyl groups in anhydroglucose units. Formula I is only used for illustrative purposes and does not represent the cellulose ethers of the invention; the substitution with hydroxyalkyl groups is not shown in Formula I.

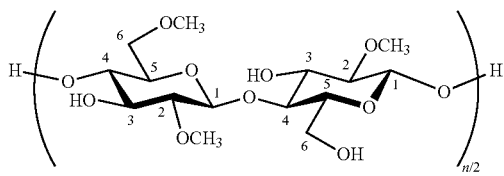

Formula I

The cellulose ether preferably has a DS(methyl) of from 1.2 to 2.2, more preferably from 1.25 to 2.10, and most preferably from 1.40 to 2.05 and particularly 1.60 to 2.05. The degree of the methyl substitution, DS(methyl), of a cellulose ether is the average number of OH groups substituted with methyl groups per anhydroglucose unit. For determining the DS(methyl), the term "OH groups substituted with methyl groups" does not only include the methylated OH groups directly bound to the carbon atoms of the cellulose backbone but also methylated OH groups that have been formed after hydroxyalkylation.

The cellulose ether has an MS(hydroxyalkyl) of 0.05 to 1.00, preferably 0.08 to 0.80, more preferably 0.12 to 0.70, most preferably 0.15 to 0.60, and particularly 0.20 to 0.40. The degree of the hydroxyalkyl substitution is described by the MS (molar substitution). The MS(hydroxyalkyl) is the average number of hydroxyalkyl groups which are bound by an ether bond per mole of anhydroglucose unit. During the hydroxyalkylation multiple substitutions can result in side chains.

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion. The DS(methyl) and MS(hydroxyethyl) in hydroxyethyl methylcellulose is effected by Zeisel cleavage with hydrogen iodide followed by gas chromatography. (G. Bartelmus and R. Ketterer, Z. Anal. Chem. 286 (1977) 161-190).

The viscosity of the cellulose ether utilized in the sustained release dosage form of the present invention preferably is generally at least 50 mPa·s, preferably from 50 to 200,000 mPa·s, more preferably from 500 to 100,000 mPa·s, most preferably from 1000 to 80,000, particularly from 1000 to 60,000, determined as a 1.5% by weight solution in water in a Haake RS600 rheometer with a cone and plate Geometry (CP-60/2°) at 20° C. and at a shear rate of 2.55 s$^{-1}$.

The onset dissolution temperature of the cellulose ether utilized in the sustained release composition of the present invention, measured at a concentration of 2 weight percent in water, is at least 40° C., preferably at least 42° C., more preferably at least 44° C., and most preferably at least 45° C. The onset dissolution temperature of the cellulose ether utilized in the sustained release dosage form of the present invention is preferably up to 70° C., more preferably up to 65° C., and most preferably up to 60° C., measured at a concentration of 2 weight percent in water. The onset dissolution temperature is a rheological characterization technique for the determination of the dissolution of the cellulose ether depending on the temperature. The onset dissolution temperature is measured as described in the Examples.

Methods of making the above described cellulose ethers are described in detail in the Examples. Some aspects of the process for making the cellulose ethers are described in more general terms below.

The cellulose ether described above can be obtained by a multistage etherification process comprising:
 a first stage comprising:
  i. treating cellulose pulp with a first amount of alkalizing agent, and
  ii. addition of at least one methylating agent to the cellulose pulp, subsequent heating of the reaction mixture to a reaction temperature of 70° C. or more and thereafter
 at least one additional stage comprising:
  iii. addition of an additional amount of alkalizing agent to the reaction mixture at a rate of less than 0.04 molar equivalents of alkalizing agent per mole of anhydroglucose units per minute, and, optionally for each individual additional stage,
  iv. addition of an additional amount of at least one methylating agent to the reaction mixture,
wherein before, after or concurrently with the addition of the alkalizing agent in the first stage at least one hydroxyalkylating agent, and optionally at least one alkylating agent different from a methylating agent, is added to the cellulose pulp, or, as the etherification of the cellulose pulp proceeds, to the partially reacted cellulose pulp.

The cellulose raw material for preparing the cellulose ether is typically cellulose pulp obtained from cotton or wood, preferably wood pulp. It is typically provided in powder or chip form.

In the above-mentioned process the cellulose pulp or, as the reaction of cellulose pulp to the hydroxyalkyl methyl cellulose proceeds, the partially reacted cellulose pulp, is alkalized in two or more stages, preferably in two or three stages, in one or more reactors with an alkalizing agent. The alkalizing agent may be any strong base such as an alkali metal hydroxide, preferably sodium hydroxide, caustic soda or lime or a mixture of more than one of such strong bases, employed as an aqueous solution. Usually an aqueous solution of an alkali metal hydroxide is employed, preferably having an alkali metal hydroxide content of from 30 to 70 percent, more preferably from 35 to 60 percent, most preferably from 48 to 52 percent, based on the total weight of the aqueous solution of the alkali metal hydroxide.

In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product.

In the first stage of the process the cellulose pulp is treated with a first amount of alkalizing agent, typically from 1.2 to 3.5 molar equivalents of alkalizing agent per mole of anhydroglucose units in the cellulose. The treatment can be conducted by any means known in the art such as by steeping in a bath or stirred tank or spraying. Uniform swelling and distribution of the alkalizing agent in the pulp may be achieved by mixing and agitation. In the first stage the rate of addition of the aqueous solution of the alkalizing agent to the cellulose pulp is not critical. It may be added in several portions, e.g. 2 to 4 portions, or continuously. During first stage alkalization, which usually lasts from 15 to 60 minutes, the temperature is typically maintained at 45° C. or below.

Moreover, a methylating agent such as methyl chloride or dimethyl sulfate is added to the cellulose pulp within the first stage of the process, before, after or concurrently with the first amount of alkalizing agent, preferably after the addition of the alkalizing agent. The methylating agent can be added to the cellulose or, as the reaction of cellulose pulp to the hydroxyalkyl methyl cellulose proceeds, to partially reacted cellulose pulp, in a single stage, but it is preferably added in two or more stages, more preferably two or three stages, most preferably two stages.

If the methylating agent is added in a single stage, it is generally added in an amount of from 3.5 to 6 mole of methylating agent per mole of anhydroglucose units, but in any event it is added in at least an equimolar amount, compared to the alkalizing agent added in the first stage, before heating the reaction mixture. If the methylating agent is added in a single stage, it is preferably added at a rate of from 0.25 to 1.0 molar equivalents of methylating agent per mole of anhydroglucose units per minute. The methylating agent used in the first stage may be pre-mixed with any conventional suspending agent. In this case, a mixture comprising from 20 to 50%, more preferably from 30 to 50%, of the suspending agent, based on the total weight of the suspending agent and the at least one methylating agent is preferably employed.

Once the cellulose has been treated with the first amount of alkalizing agent and the additions of the methylating agent and possible further components of the first stage, preferably conducted also at a temperature of 45° C. or below, have been accomplished, the reaction mixture is heated, typically within 30 to 80 minutes, to a reaction temperature of at least 70° C., preferably in the range of 70-90° C., more preferably in the range of 70-80° C. Usually the reaction is then allowed to proceed at this reaction temperature for 10 to 30 minutes.

Subsequently the process comprises at least one additional stage comprising addition of an additional amount of alkalizing agent and, optionally for each individual additional stage, addition of an additional amount of the methylating agent to the reaction mixture. The total amount of additional alkalizing agent added as aqueous solution within the at least one additional stage typically ranges from 1.0 to 2.9 molar equivalents of alkalizing agent per mole of anhydroglucose units. Preferably, the molar equivalent ratio between the amount of alkalizing agent added in the first stage and the amount of alkalizing agent added in total in the at least one additional stage is from 0.6:1 to 3.5:1. It is important to add the alkalizing agent in the at least one additional stage slowly to the reaction mixture, i.e. at a rate of less than 0.04, preferably less than 0.035, more preferably less than 0.03 molar equivalents of alkalizing agent per mole of anhydroglucose units per minute. The alkalizing agent of the second stage is generally added at a temperature of from 55 to 85° C., preferably from 60 to 80° C.

Typically the methylating agent is used in a total amount in the range of 2 to 6 moles per mole of anhydroglucose units. If the methylating agent is added not only in the first stage, but also in at least one additional subsequent stage, preferably in one additional stage, it is typically added in an amount of 2.0 to 4.0 mole of methylating agent per mole of anhydroglucose units in the first stage and in a total amount of 1.5 to 3.4 mole of methylating agent per mole of anhydroglucose units in the at least one additional stages. In any event the methylating agent is added in at least an equimolar amount, compared to the alkalizing agent present in the reaction mixture. Accordingly, the methylating agent of the second stage, if any, is added to the reaction mixture before or during the second and optionally third stage of adding the alkalizing agent in such a manner that the cellulose or, as the reaction of cellulose pulp to the hydroxyalkyl methyl cellulose proceeds, the partially reacted cellulose pulp, is continuously contacted with an at least equimolar equivalent amount of the methylating agent compared to the alkalizing agent.

If the methylating agent is added in two stages, the methylating agent of the first stage is preferably added at a rate of from 0.25 to 0.5 molar equivalents of methylating agent per mole of anhydroglucose units per minute. The methylating agent of the single stage or of the first stage may be pre-mixed with a suspending agent. In this case the mixture of suspending agent and methylating agent preferably comprises from 20 to 50 weight percent, more preferably from 30 to 50 weight percent, of the suspending agent, based on the total weight of methylating agent and suspending agent.

If the methylating agent is added in two stages, the second stage of methylating agent is generally added to the reaction mixture after having heated the reaction mixture to a temperature of about 70-90° C. for 10 to 30 minutes. The methylating agent of the second stage is preferably added at a rate of from 0.25 to 0.5 molar equivalents of methylating agent per mole of anhydroglucose units per minute. If the methylating agent is added in two stages, the molar ratio between the methylating agent of the first stage and the methylating agent of the second stage is generally from 0.68:1 to 1.33:1. The methylating agent in each of the at least one additional stage, if used therein, should be added to the reaction mixture prior to or during the addition of the additional amount of alkalizing agent of that stage in such a manner that the cellulose is continuously contacted with an at least equimolar equivalent amount of the at least one methylating agent compared to the alkalizing agent.

As an alternative to the procedure described above wherein the methylating agent and alkalizing agent each are added in two stages, the methylating agent of the second stage may be added to the reaction mixture after a portion of the alkalizing agent of the second stage has been added, followed by subsequent addition of alkalizing agent; i.e., the methylating agent is added in a second stage, which is followed by the addition of a third stage alkalizing agent. In this embodiment of the process, the total amount of alkalizing agent per mole of anhydroglucose added in the second and third stage is generally 1.0 to 2.9 moles per mole of anhydroglucose units, of which preferably 40 to 60 percent are added in the second stage and 60 to 40 percent are added in the third stage. Preferably the alkalizing agent used in the third stage is added slowly, i.e., at a rate of less than 0.04, typically at a rate of less than 0.03 molar equivalents of alkalizing agent per mole of anhydroglucose units per minute. The methylating agent and alkalizing agent of the third stage are generally added at a temperature of from 55 to 85° C., preferably from 60 to 80° C.

One or more, preferably one or two, hydroxyalkylating agents, such as ethylene oxide and/or propylene oxide are also added to the cellulose pulp, or, as the reaction of cellulose pulp to the hydroxyalkyl methyl cellulose proceeds, to partially reacted cellulose pulp, either before, after, or concurrently with the alkalizing agent added in the first stage. A single hydroxyalkylating agent or more than one, preferably only one, hydroxyalkylating agent may be utilized. The hydroxyalkylating agent is generally added in an amount of 0.2 to 2.0 mole of hydroxyalkylating agent per mole of anhydroglucose units. The hydroxyalkylating agent is advantageously added before heating the reaction mixture to the reaction temperature, i.e. at a temperature of from 20 to 70° C., preferably from 40 to 60° C.

An additional alkylating agent, different from a methylating agent, may also be added to the cellulose pulp, either before, after, or concurrently with the alkalizing agent added in the first stage. Non-limiting examples include ethyl chloride, ethyl bromide or ethyl iodide, diethyl sulphate and/or propyl chloride. The additional alkylating agent is generally added in an amount of 0.5 to 6 mole of alkylating agent per mole of anhydroglucose units. The alkylating agent is advantageously added before heating the reaction mixture to the reaction temperature, i.e. at a temperature of from 20 to 70° C., preferably from 40 to 60° C.

After accomplishment of the above described multistage etherification the obtained cellulose ether is typically further purified, dried and/or milled. Usually the cellulose ether is washed to remove salt and other reaction by-products. Any solvent in which the salt formed as a by-product of the etherification reaction is soluble may be employed, but water is usually utilized. The cellulose ether may be washed in the reactor, but is preferably washed in a separate washer located downstream of the reactor. Before or after washing, the cellulose ether may be stripped e.g. by exposure to steam to reduce the content of residual volatile organic compounds.

The cellulose ether can be dried to reduce moisture and the content of other volatile compounds to preferably 0.5 to 10.0 wt. %, more preferably 0.8 to 5.0 wt. % of water and other volatile compounds, based on the sum of the weight of the cellulose ether, water and other volatile compounds. Drying can be carried out using a conventional drier such as a tray drier, fluid bed drier, flash drier, agitation drier or tube drier. The reduced moisture and content of other volatile compounds enables the cellulose ether to be milled into particulate form. The dried cellulose ether can be milled to particulates of desired size by any suitable means known in the art such as a ball mill, an impact pulverizer, knife grinder or air-swept impact mill. If desired, drying and milling can be conducted simultaneously.

The above-described cellulose ether is useful as an excipient for a sustained-release dosage form, which means that it has the function to regulate the release of an active ingredient from the dosage form over an extended period of time. The term "sustained-release" is used herein synonymously to the terms prolonged release; extended release; sustained release; depot release; time release; controlled release; modified release or prolonged action. "Sustained release" is an approach by which active ingredients, such as biologically active compounds, are made available at a rate and duration designed to accomplish an intended effect. The above-described cellulose ethers are useful for forming at least a portion of the polymeric matrix for sustained-release dosage forms in a variety of technological fields, for example in personal care, laundry care or agricultural applications, water treatment, and particularly in human or animal health care applications, most specifically pharmaceutical applications wherein a biologically active ingredient is selected from vitamins, herbal and mineral supplements and drug substances. For example, an oral controlled release drug delivery system is a device or dosage form that regulates the release of a drug into the gastrointestinal tract, thereby controlling the absorption rate of that drug in order to achieve a desired blood plasma profile. These dosage forms are designed to provide a constant or nearly constant drug level in plasma with reduced fluctuation via a slow, continuous release of drug over an extended period of time, for example in a time period between 4 and 30 hours, preferably between 8 and 24 hours to release the active ingredient from the dosage form in its entirety.

It has been found that controlled release dosage forms, such as controlled release tablets, wherein at least a portion of the polymeric matrix is formed by at least an above-described cellulose ether remains intact without substantial disintegration over an extended time period, typically at least 4 hours, more typically at least 6 hours, and under optimized conditions at least 8 hours. Without wanting to be bound by the theory, it is believed that the above-described cellulose ether is hydrated to form a strong swollen layer on the outer skin of the dosage form upon contact with an aqueous liquid. The strong swollen layer minimizes the release of the active ingredient caused by erosion of the dosage form. Since the tablets do not disintegrate, i.e., do not fall apart to a significant extent, the release of the active ingredient is controlled by the slow dissolution of the swollen layer that has been formed by hydration of the above-described cellulose ether on the outer skin of the dosage form. A strong swollen layer also reduces the penetration of water into the controlled release dosage forms, which further delays the release of an active ingredient, particularly a water-soluble active ingredient, into an aqueous environment due to a reduced amount of a water in the zone of the dosage form into which the water diffuses and dissolves the active ingredient. When using one or more of the above-described cellulose ethers for forming at least a portion of the polymeric matrix for sustained-release dosage forms, the release of the active ingredient can be extended, as compared to known comparable cellulose ethers. Alternatively, essentially the same release of the active ingredient can be achieved as with known comparable cellulose ethers at a reduced weight of the polymeric matrix, which results in controlled release dosage forms, such as tablets, that are smaller and easier to ingest.

It is to be understood that one or more of the above-described cellulose ethers and one or more types of active ingredients can be blended with one or more optional adjuvants to prepare a dosage form. Preferably the blending process is conducted at about room temperature. Preferably one or more types of the above-described cellulose ethers form from 50 to 100 percent, more preferably from 75 to 100 percent, most preferably from 80 to 100 percent of the weight of the polymeric matrix. The amount of the one or more above-described cellulose ethers generally is at least 5 percent, preferably at least 10 percent, more preferably at least 20 percent, and most preferably at least 25 percent, based on the total weight of the dosage form, and generally up to 70 percent, preferably up to 60 percent, more preferably up to 50 percent, and most preferably up to 40 percent, based on the total weight of the dosage form.

A large variety of active ingredients are useful, dependent on the intended end-use of the dosage form. Active ingredients are known in the art and include, among others, detergents or surfactants for laundry care applications; fertilizers, herbicides or pesticides in formulations designed to release the bioactive agents over a prolonged period of time in agricultural applications. A wide range of biologically active ingredients are useful, such as vitamins, herbals and mineral supplements and drugs. The term "drug" is conventional, denoting a compound having beneficial prophylactic and/or therapeutic properties when administered to an animal, especially humans. The amount of the active ingredient generally is at least 0.5 percent, preferably at least 1 percent, more preferably at least 5 percent, most preferably at least 10 percent, based on the total weight of the dosage form, and generally up to 75 percent, preferably up to 65 percent, more preferably up to 55 percent, most preferably up to 45 percent, based on the total weight of the dosage form. In one aspect of the invention the sustained release dosage form comprises a drug of an aqueous solubility of at least 1 mg/ml, preferably of at least 5 mg/ml, or even as high as 10 to 40 mg/ml, such as paracetamol. In another aspect of the invention the sustained release dosage comprises a drug of poor aqueous solubility, i.e., a drug that has an aqueous solubility of less than 1 mg/ml, typically even less than 0.5 mg/ml. Useful low-solubility drugs are listed in the International Patent Application WO 2005/115330, pages 17-22. The aqueous solubility is measured at 25° C. in water or as phosphate buffered saline solution adjusted to a pH of 6 to 7. Useful optional adjuvants are known in the art and are generally solid, such as one or more fillers, pigments, colorants, flavorants, disintegrating agents, binders, plasticizers, salts, acidic and basic pH modifiers, antioxidants and/or lubricants. Examples of such adjuvants are acacia, corn starch, guar gum, potato starch, alginic acid, stearic acid, magnesium stearate, talcum, lactose, sucrose, dicalcium phosphate, microcrystalline cellulose, sugars, minerals, cellulose powder or cellulose fibers.

The blend is optionally granulated by a known dry or wet granulation process before it is compressed into a sustained release dosage form, such as tablets, pellets or caplets. Compression processes to produce a sustained release dosage form are known in the art. The open-ended terms "comprising," and "comprises," are synonymous with "including," "having," and "characterized by". When referring to a preceding list of elements or steps (e.g., ingredients), the phrases "combination thereof," "mixture thereof," and the like mean any two or more (at least two) up to and including all of the listed elements or steps. The term "optionally" means "with or without" (e.g., "optionally, an additive" means with or without an additive).

EXAMPLES

The following examples are for illustrative purposes only and are not intended to limit the scope of the present invention. All percentages are by weight unless otherwise specified. The properties of the cellulose ethers in the sustained release compositions of Examples 1-4 and Comparative Examples A-C are measured as follows:

Viscosity

To achieve homogenous solutions, 3 g of the cellulose ether powder (under consideration of the water content of the cellulose ether) is suspended in 197 g water at 70° C. with an overhead laboratory stirrer at 700 rpm for 10 min. These solutions are then cooled to a temperature of 2° C. for 5 hours to complete the dissolution process. During these 5 hours the solutions are stirred at 500-1000 rpm and lost water due to evaporation is replaced. These solutions are then stored in a refrigerator overnight. Prior to the analysis the cold solutions are stirred for 15 min at 100 rpm.

The viscosities of the hydroxypropyl methylcellulose is determined in a 1.5% by weight aqueous solution at 20° C. in a Haake RS600 rheometer with a cone and plate Geometry (CP-60/2°) at 20° C. and at a shear rate of 2.55 $s^{-1}$.

Determination of % Methoxyl and % Hydroxypropoxyl

The determination of the % methoxyl and % hydroxypropoxyl in hydroxypropyl methylcellulose is carried out according to the United States Pharmacopeia (USP 32). The values obtained are % methoxyl and % hydroxypropoxyl. These are subsequently converted into degree of substitution (DS) for methyl substituents and molar substitution (MS) for hydroxypropyl substituents. Residual amounts of salt have been taken into account in the conversion.

Determination of s23/s26

The determination of ether substituents in cellulose ethers is generally known and e.g., described in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 is conducted as follows:

10-12 mg of the cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the cellulose ether is performed using a dry nitrogen atmosphere in a 4 mL screw cap vial. After solubilization the dissolved cellulose ether is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 μL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 μL of acetic anhydride and 150 μL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 μm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 μL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN Increments Used for ECN Calculations:

| Type of carbon atom | ECN increment |
| --- | --- |
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of s23/s26.

MRFmonomer=ECN2,3,6-Me/ECNmonomer

The mole fractions of the monomers are calculated by dividing the corrected peak areas by the total corrected peak area according to the following formulas:

$$s23=[(23\text{-Me}+23\text{-Me-6-HAMe}+23\text{-Me-6-HA}+23\text{-Me-6-HAHAMe}+23\text{-Me-6-HAHA}]; \text{ and}$$

$$s26=[(26\text{-Me}+26\text{-Me-3-HAMe}+26\text{-Me-3-HA}+26\text{-Me-3-HAHAMe}+26\text{-Me-3-HAHA}], \text{ wherein}$$

s23 is the sum of the molar fractions of anhydroglucose units which meet the following conditions:
a) the two hydroxyl groups in the 2- and 3-positions of the anhydroglucose unit are substituted with methyl groups and the 6-position is not substituted (=23-Me); b) the two hydroxyl groups in the 2- and 3-positions of the anhydroglucose unit are substituted with methyl groups and the 6-position is substituted with methylated hydroxyalkyl (=23-Me-6-HAMe) or with a methylated side chain comprising 2 hydroxyalkyl groups (=23-Me-6-HAHAMe); and c) the two hydroxyl groups in the 2- and 3-positions of the anhydroglucose unit are substituted with methyl groups and the 6-position is substituted with hydroxyalkyl (=23-Me-6-HA) or with a side chain comprising 2 hydroxyalkyl groups (=23-Me-6-HAHA). s26 is the sum of the molar fractions of anhydroglucose units which meet the following conditions:
a) the two hydroxyl groups in the 2- and 6-positions of the anhydroglucose unit are substituted with methyl groups and the 3-position is not substituted (=26-Me);
b) the two hydroxyl groups in the 2- and 6-positions of the anhydroglucose unit are substituted with methyl groups and the 3-position is substituted with methylated hydroxyalkyl (=26-Me-3-HAMe) or with a methylated side chain comprising 2 hydroxyalkyl groups (=26-Me-3-HAHAMe); and c) the two hydroxyl groups in the 2- and 6-positions of the anhydroglucose unit are substituted with methyl groups and the 3-position is substituted with hydroxyalkyl (=26-Me-3-HA) or with a side chain comprising 2 hydroxyalkyl groups (=26-Me-3-HAHA).

The results of the determination of the substituents in the HAMC are listed in Table 4 below. In the case of HPMC's hydroxyalkyl (HA) is hydroxypropyl (HP) and methylated hydroxyalkyl (HAMe) is methylated hydroxypropyl (HPMe).

Measurement of Onset Dissolution Temperature:

The onset dissolution temperature is a rheological characterization technique for the determination of the dissolution of cellulose ethers depending on the temperature by measuring the torque build-up of the cellulose ether in water. These measurements are performed with a Haake RS1 Rheometer (Thermo Fisher Scientific, Karlsruhe). A Cup (Couette) Z-34 geometry with a wing stirrer (the diameter and the height of the stirrer plate are 30 mm each; the wing plate has 4 perforations of 5 mm diameter). The amounts of water and cellulose ether are chosen to achieve a final concentration of 2%. 58.8 g of water is added into the cup and heated up to 70° C. At this temperature 1.2 g of the cellulose ether is slowly added. At this temperature the cellulose ether is insoluble and the suspension is stirred with 500 rpm for 60 sec. After a good suspension is achieved the temperature is decreased at a fixed cooling rate of 1° C./min, while stirring with 388 rpm. The torque is recorded with 4 data points/min. starting at 70° C. and ending at a temperature at least 20° C. lower than the estimated onset dissolution temperature, resulting in a torque build-up curve as function of temperature. For the further analysis of the onset dissolution temperature the data are normalized according to the following equation:

$$M_{norm} = \frac{M - M_i}{M_{max} - M_i}$$

where M represents the measured torque at a specific temperature, $M_i$ represents the start value of torque at the highest temperature (i.e., at 70° C.) at 300 rpm and $M_{max}$ represents the final torque at the lowest temperature (i.e., at 2° C.). For analysis of the onset dissolution temperature the values of torque (y-axis) are plotted against the temperature (x-axis). Linear regressions are performed to the obtained torque values for multiple temperature increments, each increment covering 2.5° C. An increment is started every 0.1° C. The point of intersection of the linear regression with the largest slope and a sufficient correlation coefficient (at least 98.0%) with the temperature axis is called "onset dissolution temperature". FIG. 1 is a graphical representation how to determine the onset dissolution temperature of a cellulose ether.

Drug Release Determination

A matrix tablet was produced from a blend comprising 50 wt. % of the drug paracetamol as active ingredient, 30 wt. % of the hydroxypropyl methylcellulose (HPMC) of Examples 1 to 4 and Comparative Examples A to C, 18% lactose, 1% talcum and 1% magnesium stearate. The matrix tablet was produced by blending HPMC together with paracetamol and lactose for one minute. Then talcum was added to the blend and blended for one minute. At last magnesium stearate was added right before tablet pressing and blended for two minutes. Tablets of a size of 10.8 mm diameter by 3.9 mm thickness were compressed with a compression force of about 50 kN. The tabletting conditions were chosen to achieve a tablet hardness of about 80N and a tablet weight of about 400 mg.

Tablet dissolution testing was conducted using sinkers in 900 mL pH 5.7 phosphate buffer for 22 h at 37° C. with a USP dissolution apparatus (e. g. Erweka Dissolution Tester 626, Erweka GmbH) equipped with standard USP II paddles rotating at a speed of 50 rpm. The absorbance of paracetamol at each sample time was measured using a UV-Vis spectrophotometer (e.g. Shimadzu UV-1700, Shimadzu Deutschland GmbH, Duisburg, Germany) with 10 mm light path cuvettes (e.g. Hellma Präzisions Ktivette 176.700-QS, Hellma Analytics, Müllheim, Germany). The concentration of paracetamol was calculated using a standard calibration curve (0; 0.001442; 0.004326; 0.007210; 0.014420; 0.028840 gramm paracetamol/100 mL buffer) at a wavelength of 243 nm. Fresh buffer was prepared by weighing 34.03 g KH2PO4 and 0.72 g NaOH in a flask, filling up to 5 L with deionized (DI) water, and sufficiently agitating to ensure salt dissolution and solution uniformity.

Example 1

Hydroxypropyl methylcellulose (HPMC) was produced according to the following procedure. Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 mole of sodium hydroxide per mole of anhydroglucose units in the cellulose and the temperature was adjusted to 40° C. After stirring the mixture of aqueous sodium hydroxide solution and cellulose for about 20 minutes at 40° C., 1.5 mole of dimethyl ether, 2.5 mole of methyl chloride and 1.4 mole of propylene oxide per mole of anhydroglucose units were added to the reactor. The contents of the reactor were then heated in 60 min to 80° C. After having reached 80° C., the first stage reaction was allowed to proceed for 15 min.

The second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 90 min. The rate of addition was 0.026 mole of sodium hydroxide per mole of anhydroglucose units per minute. After the second stage addition was completed the contents of the reactor were kept at a temperature of 80° C. for 120 min.

After the reaction the reactor was vented and cooled down to about 50° C. The contents of the reactor were removed and transferred to a tank containing hot water. The crude HPMC was then neutralized with formic acid and washed chloride free with hot water (assessed by AgNO3 flocculation test), cooled to room temperature and dried at 55° C. in an air-swept drier. The material was then ground using an Alpine UPZ mill using a 0.5 mm screen. The particle sizes of the ground HPMC were determined by sieving. The percentage of particles passing a given mesh size was: 56%<63 µm, 80%<100 µm, 97%<200 µm, 99.9%<315 µm.

Example 2

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 mole of sodium hydroxide per mole of anhydroglucose units in the cellulose and the temperature was adjusted to 40° C. After stirring the mixture of aqueous sodium hydroxide solution and cellulose for about 20 minutes at 40° C., 1.5 mole of dimethyl ether, 2.0 mole of methyl chloride and 0.8 mole of propylene oxide per mole of anhydroglucose units were added to the reactor. The contents of the reactor were then heated in 60 min to 80° C. After having reached 80° C., the first stage reaction was allowed to proceed for 25 min.

Then the reaction was cooled down to 60° C. within 20 min. The second stage of the reaction was started by addition of methyl chloride in an amount of 2.00 molar equivalents of methyl chloride per mole of anhydroglucose units. The addition time for methyl chloride was 10 min. Then a 50 weight percent aqueous solution of sodium hydroxide at an amount of 2.00 mole of sodium hydroxide per mole of anhydroglucose units was added over a time period of 60 min. The rate of addition was 0.033 mole of sodium hydroxide per mole of anhydroglucose units per minute. After the second stage addition was completed, the contents of the reactor were heated up to 80° C. within 20 min and then kept at a temperature of 80° C. for 120 min.

After the reaction the reactor was vented and cooled down to about 50° C. The contents of the reactor were removed and further processed as described in Example 1. The percentage of particles passing a given mesh size was: 81.4%<63 µm, 98.4%<100 µm, 99.6%<200 µm, 99.9%<315 µm.

Example 3

The HPMC of Example 3 was produced as the HPMC of Example 2 except that in the first stage a 50 weight percent aqueous solution of sodium hydroxide was sprayed onto the cellulose in an amount of 3.0 mole of sodium hydroxide per mole of anhydroglucose units in the cellulose. After stirring the mixture of aqueous sodium hydroxide solution and cellulose for about 20 minutes at 40° C., 1.5 mole of dimethyl ether, 5.0 mole of methyl chloride and 1.7 mole of propylene oxide per mole of anhydroglucose units were added to the reactor. In the second stage of reaction no methyl chloride was added, but 1.00 mole of sodium hydroxide per mole of anhydroglucose units was added over a time period of 60 min. The rate of addition was 0.017 mole of sodium hydroxide per mole of anhydroglucose units per minute. The percentage of particles passing a given mesh size was: 66.3%<63 µm, 96.5%<100 µm, 99.9%<200 µm, 100%<315 µm.

Example 4

The HPMC of Example 4 was produced as the HPMC of Example 3 except that the amount of propylene oxide added to the reaction mixture was 1.6 mole of propylene oxide per mole of anhydroglucose units. The percentage of particles passing a given mesh size was: 68.8%<63 µm, 96.3%<100 µm, 99.8%<200 µm, 100%<315 µm.

Comparative Example A

The HPMC of Comparative Example A is commercially available from The Dow Chemical Company. The particle sizes of the material were determined by sieving. The percentage of particles passing a given mesh size is: 69.5%<63 µm, 99.6<150 µm, 100.0<420 µm.

Comparative Example B

Finely ground wood cellulose pulp was loaded into a jacketed, agitated reactor. The reactor was evacuated and purged with nitrogen to remove oxygen and then evacuated again. The reaction was carried out in one stage. A 50 weight percent aqueous solution of sodium hydroxide was sprayed onto the cellulose in an amount of 4.5 mole of sodium hydroxide per mole of anhydroglucose units in the cellulose and the temperature was adjusted to 40° C. After stirring the mixture of aqueous sodium hydroxide solution and cellulose for about 20 minutes at 40° C., 2.35 mole of dimethyl ether, 5.00 mole of methyl chloride and 2.05 mole of propylene oxide per mole of anhydroglucose units were added to the reactor. The contents of the reactor were then heated in 80 min to 80° C. After having reached 80° C., the reaction was allowed to proceed for 60 min.

After the reaction the reactor was vented and cooled down to about 50° C. The contents of the reactor were removed and further processed as described in Example 1. The percentage of particles passing a given mesh size was: 52.3%<63 µm, 83.6%<100 µm, 99.8%<200 µm, 100%<315 µm.

Comparative Example C

The hydroxypropyl methyl cellulose of Comparative Example C was produced as the hydroxypropyl methyl cellulose of Example 1 except that the amount of propylene oxide added to the reaction mixture was 1.15 mole of propylene oxide per mole of anhydroglucose units. Comparative Example C is not prior art. The percentage of particles passing a given mesh size was: 55%<63 µm, 78%<100 µm, 97%<200 µm, 99.9%<315 µm.

Figure 2:
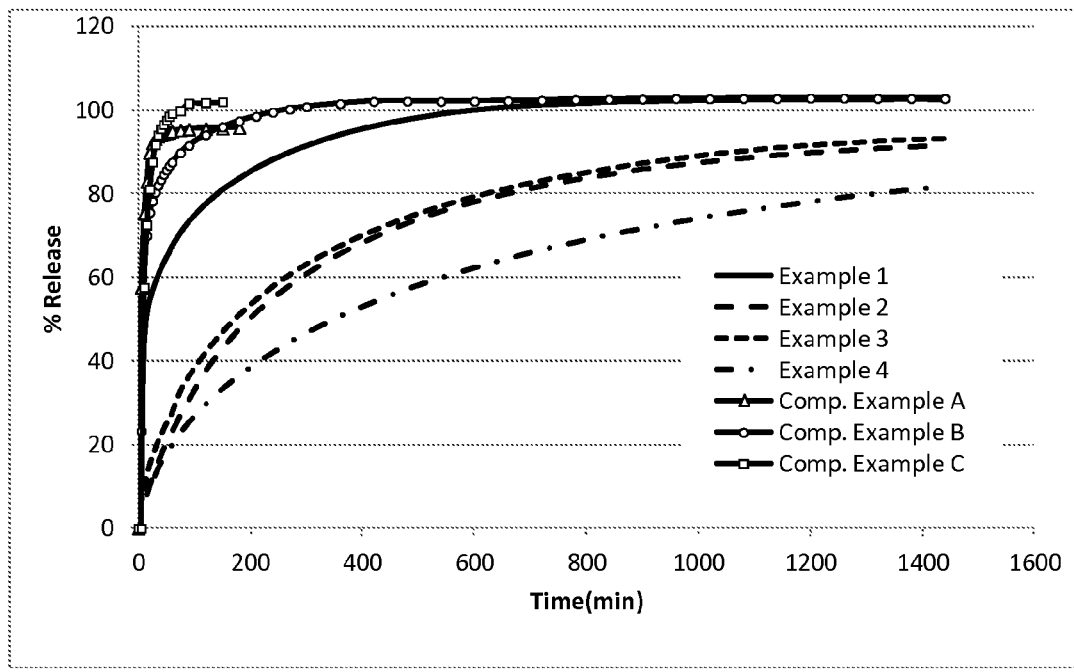
FIG. 2 is a graphical representation of a drug release from sustained release dosage forms of the present invention and of comparative dosage forms.

The properties of the hydroxypropyl methyl celluloses (HPMC) of Examples 1 to 4 and of Comparative Examples A to C are listed in Table 1 below. Details on the s23/s26 determination are listed in Table 2 below. The drug releases from sustained release dosage forms of the present invention (Examples 1-4) and of comparative dosage forms (Comparative Examples A-C) are illustrated in FIG. 2.

TABLE 1

| (Comparative) Example | DS (methyl) | MS (hydroxy-propyl) | Viscosity at 20° C. [mPa·s] | s23/s26 | s23/s26 − 0.2*MS (hydroxypropyl) | Onset dissolution temperature, [° C.] | Drug Release after 240 min [%]* |
|---|---|---|---|---|---|---|---|
| 1 | 1.86 | 0.44 | 5575 | 0.28 | 0.19 | 47.4 | 88 |
| 2 | 1.92 | 0.32 | 999 | 0.36 | 0.30 | 47.9 | 55 |
| 3 | 1.91 | 0.32 | 1290 | 0.31 | 0.25 | 46.5 | 58 |
| 4 | 1.93 | 0.30 | 2210 | 0.32 | 0.26 | 45.7 | 42 |
| A | 1.92 | 0.25 | 2690 | 0.40 | 0.35 | 45.8 | 100 |
| B | 1.82 | 0.41 | 1190 | 0.40 | 0.32 | 50.1 | 100 |
| C | 1.83 | 0.38 | 4858 | 0.27 | 0.19 | 38.5 | 100 |

*If a plateau was reached at % drug release of 95-100%, the dissolution test was stopped, since no further increase could be obtained.

TABLE 2

(HPMC)

| | (Comparative) Example | | | | | | |
|---|---|---|---|---|---|---|---|
| | 1 | 2 | 3 | 4 | A | B | C |
| DS (USP) | 1.86 | 1.92 | 1.91 | 1.93 | 1.92 | 1.82 | 1.83 |
| MS (USP) | 0.44 | 0.32 | 0.32 | 0.30 | 0.25 | 0.41 | 0.38 |
| mol fraction (26-Me) | 0.2251 | 0.2339 | 0.2349 | 0.2438 | 0.2189 | 0.2121 | 0.2374 |
| mol fraction (26-Me-3-HA) | 0.0350 | 0.0155 | 0.0308 | 0.0235 | 0.0214 | 0.0236 | 0.0316 |
| mol fraction (26-Me-3-HAHA) | 0.0000 | 0.0000 | 0.0000 | 0.0000 | 0.0000 | 0.0000 | 0.0000 |
| mol fraction (26-Me-3HAMe) | 0.0021 | 0.0039 | 0.0038 | 0.0027 | 0.0045 | 0.0045 | 0.0020 |
| mol fraction (26-Me-3HAHAMe) | 0.0000 | 0.0000 | 0.0000 | 0.0000 | 0.0000 | 0.0000 | 0.0000 |
| mol fraction (23-Me) | 0.0506 | 0.0746 | 0.0665 | 0.0699 | 0.0834 | 0.0805 | 0.0522 |
| mol fraction (23-Me-6-HA) | 0.0226 | 0.0156 | 0.0170 | 0.0165 | 0.0133 | 0.0150 | 0.0202 |
| mol fraction (23-Me-6-HAHA) | 0.0000 | 0.0000 | 0.0000 | 0.0000 | 0.0000 | 0.0000 | 0.0000 |
| mol fraction (23-Me-6-HAMe) | 0.0000 | 0.0000 | 0.0000 | 0.0000 | 0.0000 | 0.0000 | 0.0000 |
| mol fraction (23-Me-6-HAHAMe) | 0.0000 | 0.0000 | 0.0000 | 0.0000 | 0.0000 | 0.0000 | 0.0000 |
| s23/s26 | 0.28 | 0.36 | 0.31 | 0.32 | 0.40 | 0.40 | 0.27 |
| s23/s26 − 0.2*MS | 0.19 | 0.30 | 0.25 | 0.26 | 0.35 | 0.32 | 0.19 |

The drug release results shown in Table 1 and FIG. 2 illustrate that a controlled release is achieved when the polymeric matrix is formed by a cellulose ether as described further above wherein [s23/s26−0.2*MS(hydroxyalkyl)] is 0.31 or less and which has an onset dissolution temperature of at least 40° C., measured at a concentration of 2 weight percent in water. When a comparable cellulose ether was used which had a [s23/s26−0.2*MS(hydroxyalkyl)] of 0.32 or more, as in comparative Examples A and B, or which had an onset dissolution temperature of less than 40° C., a controlled release of the drug was not achieved. It should be noted that Examples 3 and 4 have very similar particle size distributions as Comparative Example A and Example 1 has a very similar particle size distribution as Comparative Examples B and C.

What is claimed is:

1. A sustained release dosage form comprising at least one active ingredient blended with a polymeric matrix, wherein at least a portion of the polymeric matrix is formed by at least one cellulose ether having an onset dissolution temperature of at least 40° C., having anhydroglucose units joined by 1-4 linkages and having methyl groups, hydroxyalkyl groups, and optionally alkyl groups being different from methyl as substituents such that
    said at least one cellulose ether has an MS (hydroxyalkyl) of 0.05 to 1.00, and
    hydroxyl groups of anhydroglucose units are substituted with methyl groups such that s23/s26−0.2*MS(hydroxyalkyl) is 0.31 or less,
    wherein s23 is the molar fraction of anhydroglucose units wherein only the two hydroxyl groups in the 2- and 3-positions of the anhydroglucose unit are substituted with a methyl group and
    wherein s26 is the molar fraction of anhydroglucose units wherein only the two hydroxyl groups in the 2- and 6-positions of the anhydroglucose unit are substituted with a methyl group, and
    wherein said at least one cellulose ether has an onset dissolution temperature of at least 40° C., measured at a concentration of 2 weight percent in water and
    wherein the amount of said at least one cellulose ether is at least 10 percent, based on the total weight of the dosage form.

2. The sustained release dosage form of claim 1 wherein said at least one cellulose ether has an onset dissolution temperature of at least 45° C.

3. The sustained release dosage form of claim 1 wherein said at least one cellulose ether is a hydroxyalkyl methyl cellulose.

4. The sustained release dosage form of claim 3 wherein said at least one cellulose ether is a hydroxypropyl methyl cellulose.

5. The sustained release dosage form of claim 1 wherein said at least one cellulose ether has a DS(methyl) of 1.2 to 2.2.

6. The sustained release dosage form of claim 5 wherein said at least one cellulose ether has a DS(methyl) of 1.60 to 2.05.

7. The sustained release dosage form of claim 1 wherein said at least one cellulose ether has an MS (hydroxyalkyl) of 0.20 to 0.40.

8. The sustained release dosage form of claim 1 wherein said at least one cellulose ether has a viscosity of at least 50 mPa·s, determined as a 1.5% by weight solution in water in a Haake rheometer at 20° C. and at a shear rate of 2.55 $s^{-1}$.

9. A process for preparing a sustained release dosage form comprising the steps of
    I.) blending one or more cellulose ethers, one or more active ingredients, and one or more optional adjuvants, and
    II.) compressing the blend to a dosage form,
    wherein at least one cellulose ether has anhydroglucose units joined by 1-4 linkages wherein the ether substituents are methyl groups, hydroxyalkyl groups, and optionally alkyl groups being different from methyl, the cellulose ether has an MS (hydroxyalkyl) of 0.05 to 1.00, and hydroxyl groups of anhydroglucose units are substituted with methyl groups such that s23/s26−0.2*MS(hydroxyalkyl) is 0.31 or less, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group, and wherein said at least one cellulose ether has an onset dissolution temperature of at least 40° C., measured at a concentration of 2 weight percent in water and wherein the amount of said at least one cellulose ether is at least 10 percent, based on the total weight of the dosage form.

10. The process of claim 9 wherein said at least one cellulose ether has an onset dissolution temperature of at least 45° C.

11. The process of claim 9 wherein said at least one cellulose ether is a hydroxyalkyl methyl cellulose.

12. The process of claim 9 wherein said at least one cellulose ether is a hydroxypropyl methyl cellulose.

13. The process of claim 9 wherein said at least one cellulose ether has a DS(methyl) of 1.60 to 2.05.

14. The process of claim 9 wherein said at least one cellulose ether has an MS (hydroxyalkyl) of 0.20 to 0.40.

15. The process of claim 9 wherein said at least one cellulose ether has a viscosity of at least 50 mPa·s, determined as a 1.5% by weight solution in water in a Haake rheometer at 20° C. and at a shear rate of 2.55 s$^{-1}$.

* * * * *